United States Patent
Ohtani et al.

(10) Patent No.: US 11,331,063 B2
(45) Date of Patent: May 17, 2022

(54) IMAGE CAPTURING APPARATUS FOR BREAST EXAMINATION

(71) Applicant: Shimadzu Corporation, Kyoto (JP)

(72) Inventors: Atsushi Ohtani, Kyoto (JP); Tetsuro Mizuta, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 438 days.

(21) Appl. No.: 16/013,118

(22) Filed: Jun. 20, 2018

(65) Prior Publication Data
US 2019/0388045 A1    Dec. 26, 2019

(51) Int. Cl.
| | |
|---|---|
| *A61B 6/00* | (2006.01) |
| *A61B 6/03* | (2006.01) |
| *A61K 51/04* | (2006.01) |
| *G06T 11/00* | (2006.01) |
| *G06T 7/00* | (2017.01) |

(52) U.S. Cl.
CPC .............. *A61B 6/502* (2013.01); *A61B 6/037* (2013.01); *A61B 6/4275* (2013.01); *A61B 6/466* (2013.01); *A61B 6/5217* (2013.01); *A61K 51/0491* (2013.01); *G06T 7/0012* (2013.01); *G06T 11/003* (2013.01); *G06T 2207/10081* (2013.01); *G06T 2207/30068* (2013.01)

(58) Field of Classification Search
CPC ....... A61B 6/502; A61B 6/037; A61B 6/4275; A61B 6/466; A61B 6/5217; A61B 6/4258; A61K 51/0491; G06T 7/0012; G06T 11/003; G06T 2207/10081; G06T 2207/30068; G16H 50/30
See application file for complete search history.

(56) References Cited

U.S. PATENT DOCUMENTS

| | | | |
|---|---|---|---|
| 10,531,846 B2* | 1/2020 | MacDonald | A61B 6/0414 |
| 2014/0119505 A1* | 5/2014 | Ohi | A61B 6/5205 378/37 |
| 2017/0116731 A1* | 4/2017 | Tsunomori | G06T 7/136 |
| 2018/0035957 A1* | 2/2018 | Liu | A61B 5/055 |
| 2019/0076108 A1* | 3/2019 | Machida | G16H 50/30 |

FOREIGN PATENT DOCUMENTS

JP    2009-072410 A    4/2009

* cited by examiner

*Primary Examiner* — Michael T Rozanski
(74) *Attorney, Agent, or Firm* — Maier & Maier, PLLC

(57) ABSTRACT

An image capturing apparatus for a breast examination in which a breakthrough mammary gland density can be adduced. A mammary gland density is calculated by recognizing a distribution of mammary gland tissues of a subject according to a distribution of radioactive pharmaceuticals distributed in a breast. An imaged image of the distribution of the radioactive pharmaceuticals is one type of function image, and represents activity in the subject. Therefore, it is possible to calculate the mammary gland density based on a mammary gland tissue of which the activity is active (an active mammary gland tissue) in the mammary gland tissues.

5 Claims, 4 Drawing Sheets

IMAGE CAPTURING APPARATUS FOR BREAST EXAMINATION

FIELD

The present invention relates to an image capturing apparatus for a breast examination imaging a distribution of radioactive pharmaceuticals in a subject by detecting a pair of annihilation radiations emitted from the subject.

BACKGROUND

In a medical institution, a radiation tomography apparatus imaging a distribution of radioactive pharmaceuticals is provided. A specific configuration of such a radiation tomography apparatus will be described. The radiation tomography apparatus of the related art includes a detector ring configured by arranging a radiation detector detecting a radiation into the shape of a circular ring. The detector ring detects a pair of radiations (a pair of annihilation radiations) in directions opposite to each other, which are emitted from radioactive pharmaceuticals in a subject (for example, refer to Patent Literature 1). Such an apparatus will be referred to as a positron emission tomography device.

There is a radiation tomography apparatus for a breast examination as one type of such radiation tomography apparatus. The image capturing apparatus for a breast examination will be described in detail. FIG. 9 is a diagram illustrating an image capturing apparatus for a breast examination of the related art. In an image capturing apparatus 51 for a breast examination of the related art, one side of a breast B of a subject M is introduced into a detector ring 62, at the time of the examination. In such a state, the detector ring 62 detects a pair of annihilation radiations emitted from the subject M.

The detector ring 62 specifies a generation source of the pair of annihilation radiations emitted from the breast B, and on the basis of position information thereof, a distribution of radioactive pharmaceuticals is generated. The radioactive pharmaceuticals have properties of being accumulated in a cancer tissue more than in a normal tissue, and thus, in a case where a distribution chart of the radioactive pharmaceuticals is diagnosed, an examination of a breast cancer can be performed.

In order to image the distribution of the radioactive pharmaceuticals, one of left and right breasts of the subject is introduced into the detector ring 62. In a case where the distribution of the radioactive pharmaceuticals in the right breast of the subject is required to be known, the right breast of the subject is introduced into the detector ring 62.

[Patent Literature 1] JP-A-2009-072410

SUMMARY

However, the image capturing apparatus for a breast examination according to the related art configuration has the following problems.

That is, the image capturing apparatus for a breast examination according to the related art configuration is not capable of sufficiently providing an index relevant to the breast.

The image capturing apparatus for a breast examination of the related art configuration is not capable of providing an index for representing the properties of the entire breast. The primary use of the image capturing apparatus for a breast examination is to image a nidus appearing in the breast. Accordingly, there is no concept of providing the index for representing the properties of the entire breast.

There is an X-ray mammography apparatus as an apparatus for imaging an abnormity of the breast. Such an apparatus is an apparatus for obtaining a shape image in the breast by irradiating the breast with an X-ray. In such an apparatus, in a case where the breast is captured, an image is obtained in which an inner structure of the entire breast vaguely appears. On such an image, a mammary gland existing in the breast is reflected. The X-ray mammography apparatus is capable of calculating a mammary gland density which is an index representing how many mammary glands are distributed in the breast. The mammary gland density indicates a ratio of the mammary gland to the total breast volume. An index such as the mammary gland density does not have characteristics of being capable of determining something, but is helpful at the time of grasping the properties of the breast. The mammary gland density is information which can be additionally obtained in an image diagnosis of the X-ray mammography apparatus, but is not capable of being obtained in a diagnosis using the image capturing apparatus for a breast examination, in the current state.

The mammary gland density of the X-ray mammography apparatus is calculated by distinguishing a mammary gland tissue from a fatty tissue according to X-ray capturing. A tissue distinguishing method is determined according to easiness of transmitting an X-ray. In a case where the mammary gland density is calculated as a help at the time of grasping the properties of the breast, there is no guarantee that such a standardized tissue distinguishing method is reasonable.

The invention has been made in consideration of such circumstances described above, and an object thereof is to provide an image capturing apparatus for a breast examination in which a breakthrough mammary gland density can be adduced.

In order to attain the object described above, the invention has the following configurations.

That is, an image capturing apparatus for a breast examination according to the invention, includes: a detector ring which is configured by arranging a radiation detector detecting a radiation into the shape of an arc, and detects a radiation derived from radioactive pharmaceuticals distributed in abreast of a subject; a three-dimensional image generating section generating a three-dimensional image representing a distribution of the radioactive pharmaceuticals in the breast, on the basis of output of the detector ring; a discriminating section which discriminates a voxel of which a pixel value is within a predetermined range in each of voxels configuring the three-dimensional image, from a breast voxel, which is a voxel belonging to the breast, and discriminates a voxel of which a pixel value is within a predetermined range in each of the voxels configuring the three-dimensional image, from a mammary gland voxel, which is a voxel positioned in a mammary gland tissue; and a mammary gland density calculating section calculating a mammary gland density by the number of breast voxels and the number of mammary gland voxels.

According to the invention, it is possible to provide an image capturing apparatus for a breast examination in which a breakthrough mammary gland density can be adduced. That is, in the invention, the mammary gland density is calculated by recognizing the distribution of the mammary gland tissues of the subject according to the distribution of the radioactive pharmaceuticals distributed in the breast. An imaged image of the distribution of the radioactive pharmaceuticals is one type of function image, and represents an activity in the subject. Therefore, according to the invention, it is possible to calculate the mammary gland density based on a mammary gland tissue of which the activity is active (an active mammary gland tissue) in the mammary gland tissues. The mammary gland density obtained according to the X-ray capturing of the related art, is calculated on the basis of the shape image, and determination of whether or not the tissue in the breast is the mammary gland, which is necessary at the time of the calculation, is performed by looks. According to the configuration of the invention, it is possible to calculate the mammary gland density representing the state of the mammary gland tissue based on the current condition in the breast, compared to the mammary gland density calculated on the basis of such a determining method.

In addition, in the image capturing apparatus for a breast examination described above, it is more desirable that the mammary gland density calculating section calculates the mammary gland density by dividing the number of voxels belonging to the breast by the number of breast voxels.

According to the configuration described above, it is possible to more reliably calculate the mammary gland density.

In addition, in the image capturing apparatus for a breast examination described above, it is more desirable that the image capturing apparatus for a breast examination, further includes: a tomographic image generating section generating a tomographic image of the three-dimensional image; an editing section performing editing of highlighting a pixel corresponding to the mammary gland voxel, in each of pixels configuring the tomographic image; and a display section displaying the tomographic image after the editing.

According to the configuration described above, it is possible to confirm authenticity of the mammary gland density.

In addition, in the image capturing apparatus for a breast examination described above, it is more desirable that the image capturing apparatus for a breast examination, further includes: an input section inputting an instruction of an operator with respect to a change in a range of a pixel value which is used when the discriminating section is operated.

According to the configuration described above, it is possible to adjust certification of the mammary gland tissue.

In addition, in the image capturing apparatus for a breast examination described above, it is more desirable that the radioactive pharmaceuticals are formed by radioactive-labelling glucose.

According to the configuration described above, it is possible to calculate the mammary gland density on the basis of an active mammary gland which more actively acts, in the mammary gland tissues.

According to the invention, it is possible to provide an image capturing apparatus for a breast examination in which a breakthrough mammary gland density can be adduced. That is, in the invention, a mammary gland density is calculated by recognizing a distribution of mammary gland tissues of a subject according to a distribution of radioactive pharmaceuticals distributed in a breast. An imaged image of the distribution of the radioactive pharmaceuticals is one type of function image, and represents activity in the subject. Therefore, it is possible to calculate the mammary gland density based on a mammary gland tissue of which the activity is active (an active mammary gland tissue) in the mammary gland tissues.

DETAILED DESCRIPTION

Hereinafter, an example of a radiation tomography apparatus according to the invention will be described with reference to the drawings. In Example 1, a γ-ray is an example of a radiation of the invention. Furthermore, a configuration of Example 1 is an image diagnosis apparatus for a breast examination. That is, a radiation tomography apparatus of Example 1 images radioactive pharmaceuticals distributed in a breast B, and generates a tomographic image. Then, the apparatus of Example 1 individually captures a right breast and a left breast of a subject M. Furthermore, the radioactive pharmaceuticals to be used for a breast examination according to the invention are formed by radioactive-labelling glucose. Therefore, the radiation tomography apparatus according to the invention images a distribution of glycometabolism activities in the breast.

Figure 1:
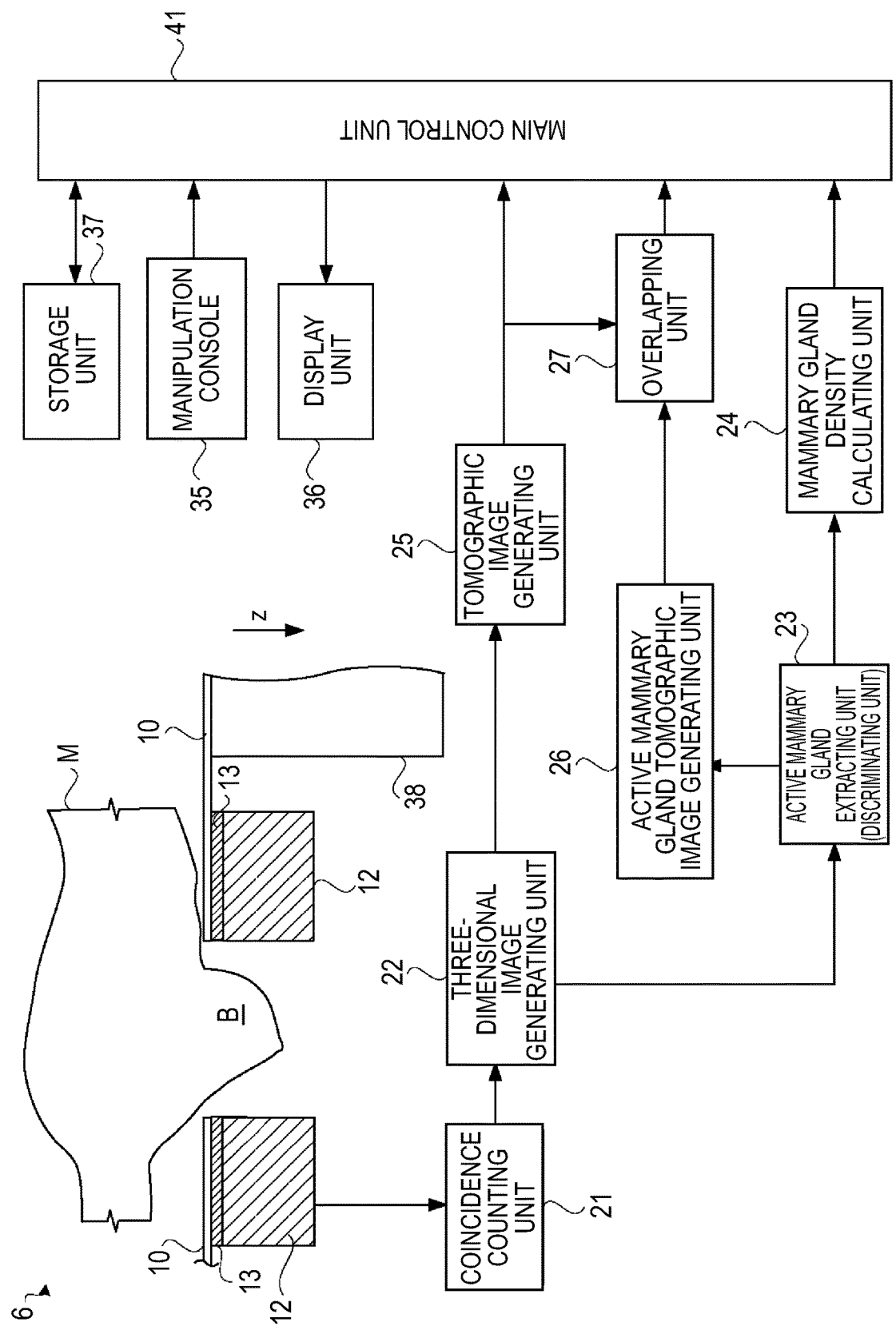
FIG. 1 is a functional block diagram illustrating an overall configuration of a radiation tomography apparatus according to Example 1.

FIG. 1 is a functional block diagram illustrating a specific configuration of the radiation tomography apparatus according to Example 1. A radiation tomography apparatus 9 according to Example 1 includes a ring-like detector ring 12 which introduces the breast B of the subject M from a z direction. An opening portion disposed in the detector ring 12 is in the shape of a cylinder (accurately, a regular decagonal column) extending in the z direction. Therefore, the detector ring 12 itself also extends in the z direction. Furthermore, a region of the opening portion of the detector ring 12 is a viewing field for capturing in which the tomographic image of the radiation tomography apparatus 9 can be generated. The z direction is directed along a direction in which a central axis of the detector ring 12 extends. The detector ring 12 is configured by arranging a radiation detector detecting a radiation, described below, into the shape of an arc. The detector ring 12 is configured by arranging the radiation detector detecting the radiation into the shape of an arc (a circular ring), and detects a radiation derived from radioactive pharmaceuticals distributed in the breast of the subject.

A top plate 10 is provided in order to place the subject M in a state where the subject M lies on the stomach. A hole into which the breast B of the subject M is inserted, is disposed on the top plate 10 to penetrate the top plate 10 in the z direction, and the breast B passes through the hole, and the breast B is introduced into the detector ring 12. The opening portion of the detector ring 12 is disposed in a vertically upward portion, and the breast B is introduced into the opening portion from a vertically downward direction.

The detector ring 12 is placed on a support base 38. A shielding plate 13 is configured of tungsten, lead, or the like (refer to FIG. 1). The radioactive pharmaceuticals also exist in a portion other than the breast B of the subject M, and thus, an annihilation γ-ray pair is generated from the portion. In a case where such an annihilation γ-ray pair generated from the portion other than a portion of interest is incident on the detector ring 12, the annihilation γ-ray pair becomes a hindrance to capture a tomographic image. Therefore, the shielding plate 13 absorbing a γ-ray is disposed into the shape of a ring, to cover one end of the detector ring 12 on a side close to the subject M in the z direction. The shielding plate 13 is disposed in a position between the top plate 10 and the detector ring 12.

In such a breast examination, fluorodeoxyglucose (FDG) is dosed to the subject. The pharmaceuticals have properties of being collected in a portion of high glycometabolism in a case of being dosed to the subject. Therefore, in a case of imaging a distribution of FPD, it is possible to know a distribution of glycometabolism in the breast of the subject.

Figure 2:
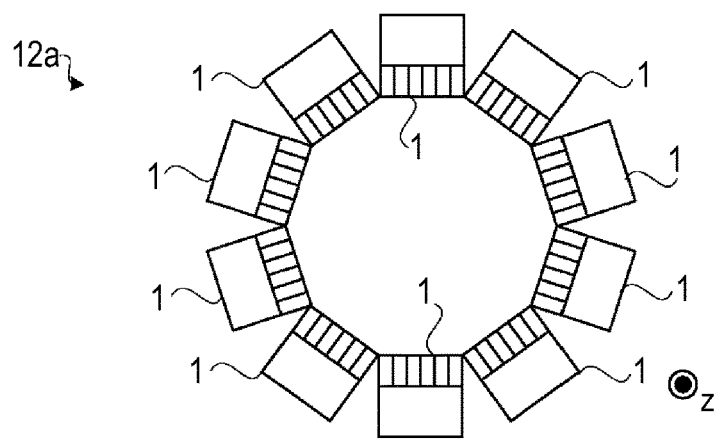
FIG. 2 is a schematic view illustrating a detector ring according to Example 1.

The configuration of the detector ring 12 will be described. In the detector ring 12, ten radiation detectors are arranged in a virtual circle on a flat surface perpendicular to the z direction (a central axis direction), and thus, one unit ring 12a is formed. Three unit rings 12a are arranged in the z direction, and thus, the detector ring 12 is configured (specifically, refer to FIG. 2).

Figure 3:
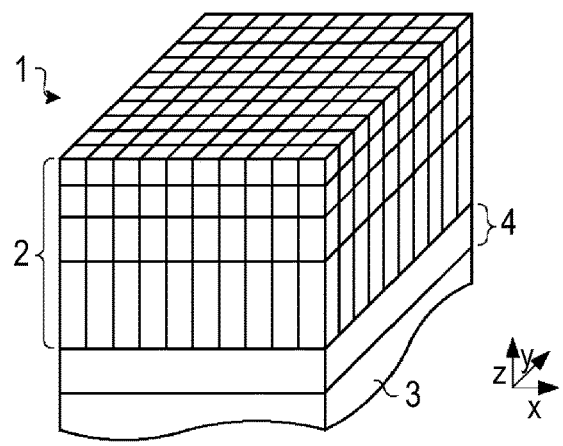
FIG. 3 is a perspective view illustrating a radiation detector according to Example 1.

The configuration of the radiation detector 1 will be simply described. FIG. 3 is a perspective view illustrating the configuration of the radiation detector according to Example 1. As illustrated in FIG. 3, a radiation detector 1 includes a scintillator 2 converting a radiation into light, and a light detector 3 configured of a photomultiplier tube detecting light. Then, a light guide 4 accepting light is provided in a position between the scintillator 2 and the light detector 3.

The scintillator 2 is configured by three-dimensionally arranging scintillator crystals. The scintillator crystal is configured of $Lu_{2(1-x)}Y_{2x}SiO_5$ in which Ce is diffused (hereinafter, referred to as LYSO). Then, the light detector 3 is capable of specifying a generation position of light, such as the scintillator crystal emitting light, and is capable of specifying a light intensity or a light generation time. In addition, the scintillator 2 of the configuration of Example 1 is merely an example of an aspect which can be adopted. Therefore, the configuration of the invention is not limited to such configuration.

A detection signal output from the detector ring 12 is sent to a coincidence counting unit 21 (refer to FIG. 1). Two γ-rays coinstantaneously incident on the detector ring 12 are an annihilation γ-ray pair caused by the radioactive pharmaceuticals in the subject. The coincidence counting unit 21 counts the number of times of detecting the annihilation γ-ray pair for each of two combinations of the scintillator crystals configuring the detector ring 12, and transmits the result to a three-dimensional image generating unit 22. The coincidence counting unit 21 determines coinstantaneousness of the detection signal by using time information applied to the detection signal according to a clock.

Figure 4:
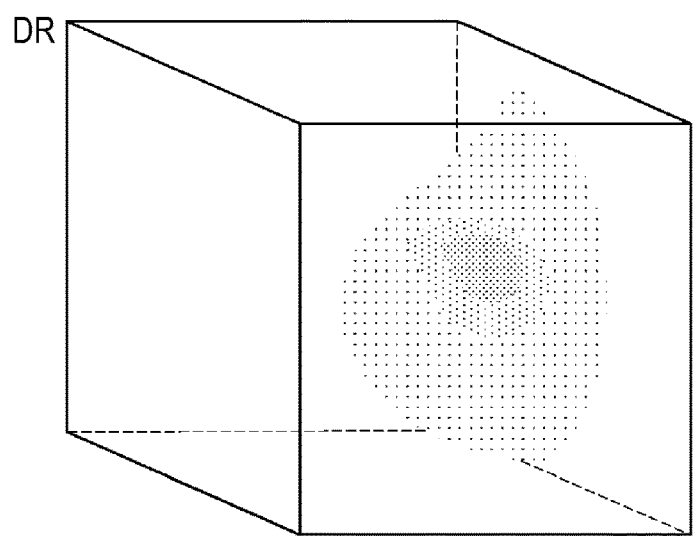
FIG. 4 is a schematic view illustrating a three-dimensional image according to Example 1.

Coincidence counting data output from the coincidence counting unit 21 is transmitted to the three-dimensional image generating unit 22. The three-dimensional image generating unit 22 generates a three-dimensional image DR in which a concentration of the radioactive pharmaceuticals is three-dimensionally mapped as illustrated in FIG. 4, on the basis of the coincidence counting data. One side of the breast of the subject is reflected in the three-dimensional image DR. The three-dimensional image generating unit 22 generates the three-dimensional image DR representing the distribution of the radioactive pharmaceuticals in the breast, on the basis of the output of the detector ring 12. The three-dimensional image generating unit 22 corresponds to the three-dimensional image generating section of the invention.

<Characteristic Configuration of Invention>

The characteristics of the invention are in a configuration where the amount of active mammary gland is calculated on the basis of the three-dimensional image DR. The active mammary gland will be described. The breast is configured of a skin, a fatty tissue, and a mammary gland tissue. Among them, the mammary gland tissue includes an active mammary gland which actively performs metabolism and acts by receiving a stimulus according to a hormone, and a non-active mammary gland which stops an action and does not function any more. The active mammary gland actively performs the glycometabolism, and thus, tends to actively absorb the radioactive pharmaceuticals. On the other hand, the non-active mammary gland or the fatty tissue rarely performs the glycometabolism, and is difficult to absorb the radioactive pharmaceuticals. Activeness of the glycometabolism in the breast is imaged in the three-dimensional image DR, and thus, it is possible to distinguish the active mammary gland from the other tissue. Such distinguishment is executed by an active mammary gland extracting unit 23. The active mammary gland extracting unit 23 corresponds to the discriminating section of the invention.

<Active Mammary Gland Extracting Unit>

Figure 5:
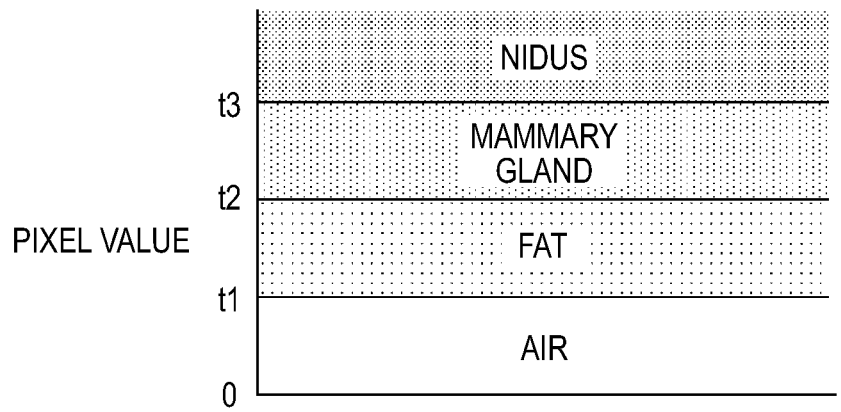
FIG. 5 is a schematic view illustrating an operation of an active mammary gland extracting unit according to Example 1.

The three-dimensional image DR generated by the three-dimensional image generating unit 22 is transmitted to the active mammary gland extracting unit 23. Three threshold values of t1, t2, and t3, as illustrated in FIG. 5, are set in the active mammary gland extracting unit 23. The active mammary gland extracting unit 23 determines what is imprinted by a voxel by comparing a pixel value of each of voxels configuring the three-dimensional image DR with the threshold value.

When the pixel value of the voxel is greater than or equal to 0 and less than the threshold value t1, the voxel imprints the air. Therefore, when the pixel value of the voxel is greater than or equal to t1, the active mammary gland extracting unit 23 determines that the voxel imprints the breast. The active mammary gland extracting unit 23 discriminates a voxel of which a pixel value is within a predetermined range in each of voxels configuring the three-dimensional image, from a breast voxel, which is a voxel belonging to the breast.

When the pixel value of the voxel is greater than or equal to t1 and less than the threshold value t2, the voxel imprints the fatty tissue or the non-active mammary gland. In addition, when the pixel value of the voxel is greater than or equal to t3, the voxel imprints a nidus. The nidus, for example, is a cancer tissue relevant to a breast cancer, and abnormally actively performs cell division. Therefore, the tissue requires more sugar, and thus, absorbs considerable radioactive pharmaceuticals. Such a tissue is not obviously a normal active mammary gland.

Therefore, when the pixel value of the voxel is greater than or equal to t2 and less than the threshold value t3, the active mammary gland extracting unit 23 determines that the voxel imprints the active mammary gland. The active mammary gland extracting unit 23 discriminates a voxel of which a pixel value is within a predetermined range in each of the voxels configuring the three-dimensional image, from a mammary gland voxel, which is a voxel positioned in the mammary gland tissue.

Figure 6:
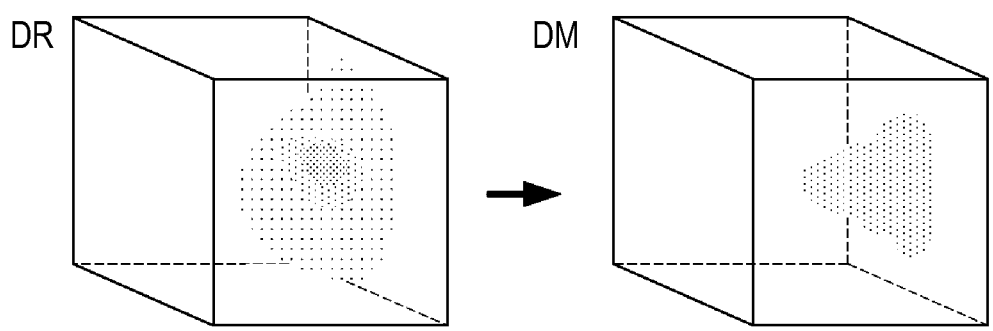
FIG. 6 is a schematic view illustrating the operation of the active mammary gland extracting unit according to Example 1.

As illustrated in FIG. 6, the active mammary gland extracting unit 23 generates an active mammary gland three-dimensional image DM representing a distribution of the voxels according to the active mammary gland on the three-dimensional image DR, on the basis of the determination using the threshold value described above.

The active mammary gland three-dimensional image DM can be displayed through a display unit 36, and thus, such display of the active mammary gland three-dimensional image DM will be described. The active mammary gland three-dimensional image DM is transmitted to an active mammary gland tomographic image generating unit 26. On the other hand, the three-dimensional image DR is transmitted to a tomographic image generating unit 25. The active mammary gland tomographic image generating unit 26 generates an active mammary gland tomographic image, which is a tomographic image at the time of cutting the active mammary gland three-dimensional image DM on a certain cut surface. Then, the tomographic image generating unit 25 generates a breast tomographic image at the time of cutting the three-dimensional image DR on the same cut surface. The active mammary gland tomographic image and the breast tomographic image are transmitted to an overlapping unit 27. The overlapping unit 27 allows the active mammary gland tomographic image to overlap with the breast tomographic image, and generates an overlapping image as illustrated on a left side of FIG. 7. The overlapping image is an image in which an active mammary gland region, which is a distribution region of the active mammary glands, is superposition-displayed on the tomographic image of the breast. Accordingly, an operator is capable of grasping on which site of the breast the apparatus certifies that there is an active mammary gland region. Such display can be used for confirming authenticity of a mammary gland density described below. This will be described below. The overlapping unit 27 corresponds to the editing section of the invention. The overlapping unit 27 performs editing of highlighting a pixel corresponding to the mammary gland voxel, in each of pixels configuring the tomographic image.

Furthermore, a cutting portion of the active mammary gland three-dimensional image DM at the time of generating the overlapping image can be changed according to input of an instruction of the operator through a manipulation console 35. According to the input of the instruction, the active mammary gland tomographic image generating unit 26 changes a cutting position, and regenerates the active mammary gland tomographic image. The tomographic image generating unit 25 regenerates the breast tomographic image of which a cutting position is identical to the cutting position of the active mammary gland tomographic image according to the operation. Each of the regenerated images is transmitted to the overlapping unit 27, and is processed to the overlapping image, and then, is displayed on the display unit 36. The manipulation console 35 corresponds to the input section of the invention.

Figure 7:
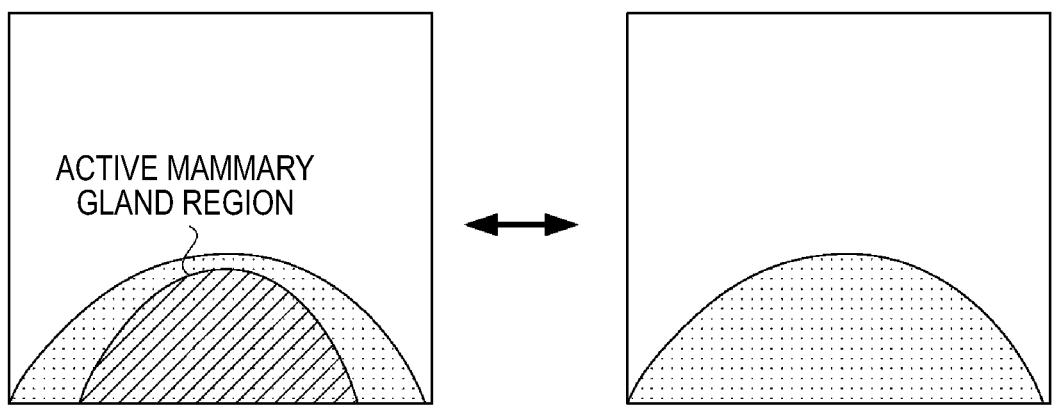
FIG. 7 is a schematic view illustrating a superimposed image according to Example 1.

In addition, the operator inputs the instruction through the manipulation console 35, and thus, the breast tomographic image up to overlapping processing can be displayed on the display unit 36, as illustrated on a right side of FIG. 7. In a case where the superimposed image can be displayed on the display unit 36 through the manipulation console 35 as illustrated on the left side of FIG. 7, the operator is capable of displaying the breast tomographic image as illustrated on the right side of FIG. 7.

<Mammary Gland Density Calculating Unit>

A determination result of the voxels configuring the three-dimensional image DR executed by the active mammary gland extracting unit 23, is transmitted to the mammary gland density calculating unit 24. The mammary gland density calculating unit 24 calculates a mammary gland density D by using the number of voxels (mammary gland voxels) Nb determined by the active mammary gland extracting unit 23 as the active mammary gland tissue and the number of voxels (breast voxels) Na determined as other than the air. Therefore, the number of voxels Nb indicates the number of voxels of which a pixel value is greater than or equal to t2 and less than the threshold value t3, on the three-dimensional image DR, and the number of voxels Na indicates the number of voxels of which a pixel value is greater than or equal to t1, on the three-dimensional image DR. The mammary gland density D is identical to Nb/Na× 100%. The mammary gland density calculating unit 24 calculates the mammary gland density by dividing the number of voxels belonging to the breast by the number of breast voxels.

Furthermore, this apparatus is capable of confirming how the mammary gland density D is calculated by considering which site of the breast as the mammary gland (refer to FIG. 7). The position of the mammary gland is distributed in the vicinity of the center of the breast. Therefore, in a case where it is confirmed that the active mammary gland is distributed in the center of the breast in the superimposed image, it is possible to evaluate that the mammary gland density D has high authenticity. The mammary gland density calculating unit 24 corresponds to the mammary gland density calculating section of the invention.

Figure 8:
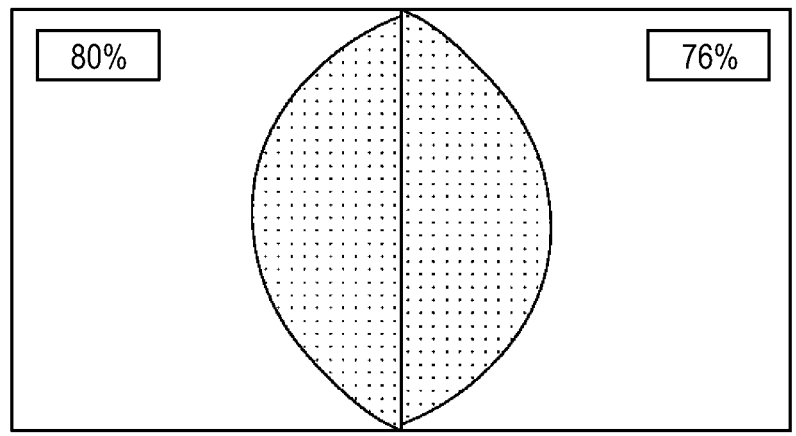
FIG. 8 is a schematic view illustrating display of a mammary gland density according to Example 1.
Figure 9:
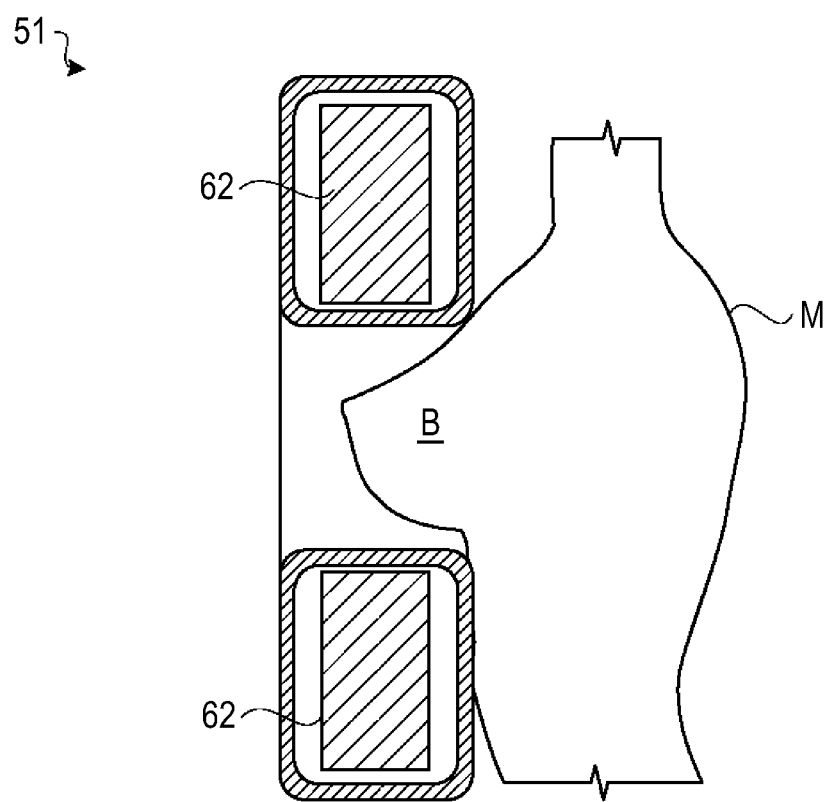
FIG. 9 is a schematic view illustrating a radiation tomography apparatus according to a configuration of the related art.

FIG. 8 illustrates a state where a breast density is displayed on the display unit 36. In a case of FIG. 8, the capturing of both breasts of the subject is ended, and the breast tomographic images of the right breast and the left breast are displayed at one time. In the display unit 36, the mammary gland density according to the right breast is superposition-displayed on the breast tomographic image according to the right breast, and the mammary gland density according to the left breast is superposition-displayed on the breast tomographic image according to the left breast.

A main control unit 41 is realized by a CPU, and executes a program for realizing each of the units 21, 22, 23, 24, 25, 26, and 27. Parameters necessary for operating each of the units are stored in a storage unit 37. In addition, an arithmetic device individually realizing each of the units may be provided instead of the main control unit 41.

As described above, according to the invention, it is possible to provide an image capturing apparatus for a breast examination in which a breakthrough mammary gland density can be adduced. That is, in the invention, a mammary gland density is calculated by recognizing a distribution of mammary gland tissues of a subject according to a distribution of radioactive pharmaceuticals distributed in a breast. An imaged image of the distribution of the radioactive pharmaceuticals is one type of function image, and represents activity in the subject. Therefore, according to the invention, it is possible to calculate the mammary gland density based on a mammary gland tissue of which the activity is active (an active mammary gland tissue) in the mammary gland tissues. The mammary gland density obtained according to the X-ray capturing of the related art, is calculated on the basis of the shape image, and determination of whether or not the tissue in the breast is the mammary gland, which is necessary at the time of the calculation, is performed by looks. According to the configuration of the invention, it is possible to calculate the mammary gland density representing the state of the mammary gland tissue based on the current condition in the breast, compared to the mammary gland density calculated on the basis of such a determining method.

The invention is not limited to the example described above, and can be modified as follows.

(1) An instruction of the operator for changing the range of the pixel value which is used when the active mammary gland extracting unit 23 is operated, may be input into the manipulation console 35. According to such a configuration, each of the threshold values t1, t2, and t3 described above can be changed according to the intention of the operator.

(2) The detector ring 12 according to Example 1 is in the shape of a circular ring, but the invention is not limited thereto. The detector ring 12 can be formed in the shape of a circular arc.

The invention claimed is:

1. An image capturing apparatus for a breast examination, comprising:
   a detector ring which is configured by arranging a radiation detector detecting a radiation into the shape of an arc, and detects a radiation derived from radioactive pharmaceuticals distributed in a breast of a subject; and
   one or more processors, configured to:
   generate a three-dimensional image representing a distribution of the radioactive pharmaceuticals in the breast, on the basis of output of the detector ring;
   discriminate a voxel of which a value corresponding to a concentration of the radioactive pharmaceuticals is within a first predetermined range in each of voxels configuring the three-dimensional image, as a breast voxel, which is a voxel belonging to the breast, and discriminate a voxel of which a value corresponding to a concentration of the radioactive pharmaceuticals is within a second predetermined range in each of the voxels configuring the three-dimensional image, the second predetermined range being larger than a third predetermined range indicating a fatty tissue, as an active mammary gland voxel, which is a voxel positioned in an active mammary gland tissue; and
   calculate an active mammary gland density, indicating a ratio of the active mammary gland tissue to the total breast volume, by the number of breast voxels and the number of active mammary gland voxels.

2. The image capturing apparatus for a breast examination according to claim 1,
   wherein the one or more processors are further configured to calculate the active mammary gland density by dividing the number of active mammary gland voxels by the number of breast voxels.

3. The image capturing apparatus for a breast examination according to claim 1, further comprising:
   a display section,
   wherein the one or more processors are further configured to:
   generate a tomographic image of the three-dimensional image;
   perform editing of highlighting a pixel corresponding to the active mammary gland voxel, in each of pixels configuring the tomographic image; and
   the display section displays the tomographic image after the editing.

4. The image capturing apparatus for a breast examination according to claim 1, further comprising:
   an input section inputting an instruction of an operator with respect to a change in a range of a value, corresponding to a concentration of the radioactive pharmaceuticals, which is used when discriminating a voxel.

5. The image capturing apparatus for a breast examination according to claim 1,
   wherein the radioactive pharmaceuticals are formed by radioactive-labelling glucose.

* * * * *